(12) United States Patent
Collins

(10) Patent No.: US 7,425,216 B2
(45) Date of Patent: Sep. 16, 2008

(54) SYSTEM AND METHOD FOR TREATING CARDIAC ARREST AND MYOCARDIAL INFARCTION

(75) Inventor: Kenneth A. Collins, Mission Viejo, CA (US)

(73) Assignee: Alsius Corporation, Irvine, CA (US)

( * ) Notice: Subject to any disclaimer, the term of this patent is extended or adjusted under 35 U.S.C. 154(b) by 599 days.

(21) Appl. No.: 11/068,954

(22) Filed: Mar. 1, 2005

(65) Prior Publication Data

US 2006/0200215 A1    Sep. 7, 2006

(51) Int. Cl.
*A61F 7/12* (2006.01)
(52) U.S. Cl. .................. 607/105; 607/104; 607/106
(58) Field of Classification Search .................. 607/96, 607/104–114
See application file for complete search history.

(56) References Cited

U.S. PATENT DOCUMENTS

| | | | |
|---|---|---|---|
| 5,755,690 A | 5/1998 | Saab | 604/96 |
| 5,837,003 A | 11/1998 | Ginsburg | 607/106 |
| 5,879,329 A | 3/1999 | Ginsburg | 604/93 |
| 5,989,238 A | 11/1999 | Ginsburg | 604/93 |
| 6,004,289 A | 12/1999 | Saab | 604/96 |
| 6,019,783 A | 2/2000 | Philips | 607/105 |
| 6,042,559 A | 3/2000 | Dobak | 604/7 |
| 6,096,068 A | 8/2000 | Dobak | 607/105 |
| 6,110,168 A | 8/2000 | Ginsburg | 606/27 |
| 6,126,684 A | 10/2000 | Gobin | 607/113 |
| 6,146,411 A | 11/2000 | Noda | 607/105 |
| 6,149,670 A | 11/2000 | Worthen | 607/3 |
| 6,149,673 A | 11/2000 | Ginsburg | 607/96 |
| 6,149,676 A | 11/2000 | Ginsburg | 607/106 |
| 6,149,677 A | 11/2000 | Dobak | 607/106 |
| 6,165,207 A | 12/2000 | Balding | 607/105 |
| 6,224,624 B1 | 5/2001 | Lasheras | 607/105 |
| 6,231,594 B1 | 5/2001 | Dae | 607/96 |
| 6,231,595 B1 | 5/2001 | Dodak | 607/106 |
| 6,235,048 B1 | 5/2001 | Dobak | 607/104 |
| 6,238,428 B1 | 5/2001 | Werneth | 607/105 |
| 6,245,095 B1 | 6/2001 | Dobak | 607/105 |
| 6,251,129 B1 | 6/2001 | Dobak | 607/105 |
| 6,251,130 B1 | 6/2001 | Dobak | 607/105 |
| 6,254,626 B1 | 7/2001 | Dobak | 607/105 |
| 6,264,679 B1 | 7/2001 | Keller | 607/105 |
| 6,287,326 B1 | 9/2001 | Pecor | 607/105 |
| 6,290,717 B1 | 9/2001 | Philips | 607/113 |
| 6,299,599 B1 | 10/2001 | Pham | 604/113 |
| 6,306,161 B1 | 10/2001 | Ginsburg | 607/106 |
| 6,312,452 B1 | 11/2001 | Dobak | 607/105 |
| 6,325,818 B1 | 12/2001 | Werneth | 607/105 |
| 6,338,727 B1 | 1/2002 | Noda | 604/113 |
| 6,364,899 B1 | 4/2002 | Dobak | 607/113 |
| 6,368,304 B1 | 4/2002 | Aliberto | 604/113 |
| 6,379,378 B1 | 4/2002 | Werneth | 607/96 |
| 6,383,210 B1 | 5/2002 | Magers et al. | 607/105 |
| 6,393,320 B2 | 5/2002 | Lasersohn | 607/3 |
| 6,405,080 B1 | 6/2002 | Lasersohn | 607/3 |
| 6,409,747 B1 | 6/2002 | Gobin | 607/113 |
| 6,416,533 B1 | 7/2002 | Gobin | 607/113 |

(Continued)

*Primary Examiner*—Roy D Gibson
(74) *Attorney, Agent, or Firm*—John L. Rogitz

(57) ABSTRACT

A closed loop heat exchange catheter can be placed in a patient suffering from cardiac arrest or myocardial infarction to cool the patient. Or, a heat exchange pad can be placed against the patient's skin to cool the patient. Magnesium sulfate is infused into the patient.

7 Claims, 2 Drawing Sheets

U.S. PATENT DOCUMENTS

| | | | |
|---|---|---|---|
| 6,419,643 B1 | 7/2002 | Shimada | 600/323 |
| 6,428,563 B1 | 8/2002 | Keller | 607/105 |
| 6,432,124 B1 | 8/2002 | Worthen | 607/105 |
| 6,436,130 B1 | 8/2002 | Philips | 607/105 |
| 6,436,131 B1 | 8/2002 | Ginsburg | 607/106 |
| 6,440,158 B1 | 8/2002 | Saab | 604/105 |
| 6,447,474 B1 | 9/2002 | Balding | 604/66 |
| 6,450,987 B1 | 9/2002 | Kramer | 604/523 |
| 6,450,990 B1 | 9/2002 | Walker | 604/113 |
| 6,451,045 B1 | 9/2002 | Walker | 607/105 |
| 6,454,792 B1 | 9/2002 | Noda et al. | 607/105 |
| 6,454,793 B1 | 9/2002 | Evans | 607/105 |
| 6,458,150 B1 | 10/2002 | Evans | 607/105 |
| 6,460,544 B1 | 10/2002 | Worthen | 607/105 |
| 6,464,716 B1 | 10/2002 | Dobak | 607/105 |
| 6,468,296 B1 | 10/2002 | Dobak | 607/105 |
| 6,471,717 B1 | 10/2002 | Dobak | 607/105 |
| 6,475,231 B2 | 11/2002 | Dobak | 607/105 |
| 6,478,811 B1 | 11/2002 | Dobak | 607/105 |
| 6,478,812 B2 | 11/2002 | Dobak | 607/105 |
| 6,482,226 B1 | 11/2002 | Dobak | 607/104 |
| 6,491,039 B1 | 12/2002 | Dobak | 128/898 |
| 6,491,716 B2 | 12/2002 | Dobak | 607/105 |
| 6,494,903 B2 | 12/2002 | Pecor | 607/105 |
| 6,497,721 B2 | 12/2002 | Ginsburg | 607/106 |
| 6,516,224 B2 | 2/2003 | Lasersohn | 607/3 |
| 6,520,933 B1 | 2/2003 | Evans | 604/103.07 |
| 6,527,798 B2 | 3/2003 | Ginsburg | 607/106 |
| 6,529,775 B2 | 3/2003 | Whitebook | 607/100 |
| 6,530,946 B1 | 3/2003 | Noda | 607/113 |
| 6,533,804 B2 | 3/2003 | Dobak | 607/105 |
| 6,540,771 B2 | 4/2003 | Dobak | 607/105 |
| 6,544,282 B1 | 4/2003 | Dae | 607/105 |
| 6,551,349 B2 | 4/2003 | Lasheras | 607/105 |
| 6,554,797 B1 | 4/2003 | Worthen | 604/113 |
| 6,558,412 B2 | 5/2003 | Dobak | 607/105 |
| 6,572,538 B2 | 6/2003 | Takase | 600/140 |
| 6,572,638 B1 | 6/2003 | Dae et al. | 607/96 |
| 6,572,640 B1 | 6/2003 | Balding | 607/105 |
| 6,576,001 B2 | 6/2003 | Werneth | 607/96 |
| 6,576,002 B2 | 6/2003 | Dobak | 607/105 |
| 6,581,403 B2 | 6/2003 | Whitebook | 62/434 |
| 6,582,398 B1 | 6/2003 | Worthen | 604/113 |
| 6,582,455 B1 | 6/2003 | Dobak | 607/105 |
| 6,582,457 B2 | 6/2003 | Dae | 607/113 |
| 6,585,692 B1 | 7/2003 | Worthen | 604/113 |
| 6,585,752 B2 | 7/2003 | Dobak | 607/105 |
| 6,589,271 B1 | 7/2003 | Tzeng | 607/113 |
| 6,595,967 B2 | 7/2003 | Kramer | 604/523 |
| 6,599,312 B2 | 7/2003 | Dobak | 607/105 |
| 6,602,243 B2 | 8/2003 | Noda | 604/544 |
| 6,602,276 B2 | 8/2003 | Dobak | 607/105 |
| 6,607,517 B1 | 8/2003 | Dae | 604/31 |
| 6,610,083 B2 | 8/2003 | Keller | 607/105 |
| 6,620,130 B1 | 9/2003 | Ginsburg | 604/113 |
| 6,620,131 B2 | 9/2003 | Pham | 604/113 |
| 6,620,188 B1 | 9/2003 | Ginsburg | 607/106 |
| 6,620,189 B1 | 9/2003 | MacHold | 607/106 |
| 6,623,516 B2 | 9/2003 | Saab | 607/105 |
| 6,635,076 B1 | 10/2003 | Ginsburg | 607/106 |
| 6,641,602 B2 | 11/2003 | Balding | 607/105 |
| 6,641,603 B2 | 11/2003 | Walker | 607/105 |
| 6,645,234 B2 | 11/2003 | Evans | 607/113 |
| 6,648,906 B2 | 11/2003 | Lasheras | 607/105 |
| 6,648,908 B2 | 11/2003 | Dobak | 607/105 |
| 6,652,565 B1 | 11/2003 | Shimada | 607/113 |
| 6,656,209 B1 | 12/2003 | Ginsburg | 607/106 |
| 6,660,028 B2 | 12/2003 | Magers | 607/105 |
| 6,673,098 B1 | 1/2004 | MacHold | 607/106 |
| 6,676,688 B2 | 1/2004 | Dobak | 607/105 |
| 6,676,689 B2 | 1/2004 | Dobak | 607/105 |
| 6,676,690 B2 | 1/2004 | Werneth | 607/105 |
| 6,679,906 B2 | 1/2004 | Hammack | 607/105 |
| 6,679,907 B2 | 1/2004 | Dobak | 607/105 |
| 6,682,551 B1 | 1/2004 | Worthen | 607/105 |
| 6,685,732 B2 | 2/2004 | Kramer | 607/106 |
| 6,685,733 B1 | 2/2004 | Dae | 607/105 |
| 6,692,488 B2 | 2/2004 | Dobak | 606/21 |
| 6,692,519 B1 | 2/2004 | Hayes | 607/105 |
| 6,695,873 B2 | 2/2004 | Dobak | 607/105 |
| 6,695,874 B2 | 2/2004 | MacHold | 607/106 |
| 6,699,268 B2 | 3/2004 | Kordis | 607/113 |
| 6,702,783 B1 | 3/2004 | Dae | 604/113 |
| 6,702,839 B1 | 3/2004 | Dae | 607/96 |
| 6,702,840 B2 | 3/2004 | Keller | 607/105 |
| 6,702,841 B2 | 3/2004 | Nest | 607/105 |
| 6,702,842 B2 | 3/2004 | Dobak | 607/105 |
| 6,706,060 B2 | 3/2004 | Tzeng | 607/105 |
| 6,709,448 B2 | 3/2004 | Walker | 607/105 |
| 6,716,188 B2 | 4/2004 | Noda | 604/6.13 |
| 6,716,236 B1 | 4/2004 | Tzeng | 607/113 |
| 6,719,723 B2 | 4/2004 | Werneth | 604/113 |
| 6,719,724 B1 | 4/2004 | Walker | 604/113 |
| 6,719,779 B2 | 4/2004 | Daoud | 607/105 |
| 6,726,653 B2 | 4/2004 | Noda | 604/113 |
| 6,726,708 B2 | 4/2004 | Lasheras | 607/105 |
| 6,726,710 B2 | 4/2004 | Worthen | 607/105 |
| 6,733,517 B1 | 5/2004 | Collins | 607/105 |
| 6,740,109 B2 | 5/2004 | Dobak | 607/105 |
| 6,749,585 B2 | 6/2004 | Aliberto | 604/113 |
| 6,749,625 B2 | 6/2004 | Pompa | 607/105 |
| 6,752,786 B2 | 6/2004 | Callister | 604/113 |
| 6,755,850 B2 | 6/2004 | Dobak | 607/104 |
| 6,755,851 B2 | 6/2004 | Noda | 607/113 |
| 2001/0007951 A1 | 7/2001 | Dobak | 607/106 |
| 2001/0016764 A1 | 8/2001 | Dobak, III | 607/105 |
| 2001/0041923 A1 | 11/2001 | Dobak | 607/105 |
| 2002/0007203 A1 | 1/2002 | Gilmartin | 607/105 |
| 2002/0016621 A1 | 2/2002 | Werneth | 607/96 |
| 2002/0068964 A1 | 6/2002 | Dobak | 607/113 |
| 2002/0077680 A1 | 6/2002 | Noda | 600/549 |
| 2002/0091429 A1 | 7/2002 | Dobak | 607/105 |
| 2002/0111616 A1 | 8/2002 | Dea | 606/27 |
| 2002/0151946 A1 | 10/2002 | Dobak, III | 607/105 |
| 2002/0177804 A1 | 11/2002 | Saab | 607/105 |
| 2002/0183692 A1 | 12/2002 | Callister | 604/113 |
| 2002/0193738 A1 | 12/2002 | Adzich | 604/113 |
| 2002/0193853 A1 | 12/2002 | Worthen | 607/3 |
| 2002/0193854 A1 | 12/2002 | Dobak | 607/105 |
| 2003/0078641 A1 | 4/2003 | Dobak | 607/105 |
| 2003/0114835 A1 | 6/2003 | Noda | 604/544 |
| 2003/0144714 A1 | 7/2003 | Dobak | 607/104 |
| 2003/0187489 A1 | 10/2003 | Dobak | 607/105 |
| 2003/0195465 A1 | 10/2003 | Worthen | 604/113 |
| 2003/0195466 A1 | 10/2003 | Pham | 604/113 |
| 2003/0195597 A1 | 10/2003 | Keller | 607/105 |
| 2003/0216799 A1 | 11/2003 | Worthen | 606/27 |
| 2003/0225336 A1 | 12/2003 | Callister | 600/505 |
| 2004/0034399 A1 | 2/2004 | Ginsburg | 607/106 |
| 2004/0039431 A1 | 2/2004 | Machold | |
| 2004/0044388 A1 | 3/2004 | Pham | 607/105 |
| 2004/0050154 A1 | 3/2004 | Machold | |
| 2004/0054325 A1 | 3/2004 | Ginsburg | 604/113 |
| 2004/0073280 A1 | 4/2004 | Dae | |
| 2004/0087934 A1 | 5/2004 | Dobak | |
| 2004/0102825 A1 | 5/2004 | Daound | |
| 2004/0102826 A1 | 5/2004 | Lasheras | |
| 2004/0102827 A1 | 5/2004 | Werneth | |
| 2004/0106969 A1 | 6/2004 | Dobak | |

| | | | |
|---|---|---|---|
| 2004/0111138 A1 | 6/2004 Bleam ................ 607/105 | 2004/0133256 A1* | 7/2004 Callister ............... 607/105 |
| 2004/0116987 A1 | 6/2004 Magers | 2004/0267339 A1 | 12/2004 Yon et al. |
| 2004/0116988 A1 | 6/2004 Hammack | 2005/0065583 A1* | 3/2005 Voorhees et al. .......... 607/104 |
| 2004/0127851 A1 | 7/2004 Noda ................. 604/503 | * cited by examiner | |

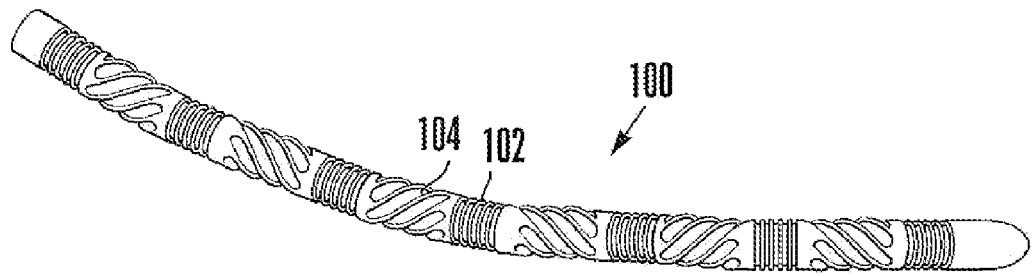
FIG. 2
FIG. 3
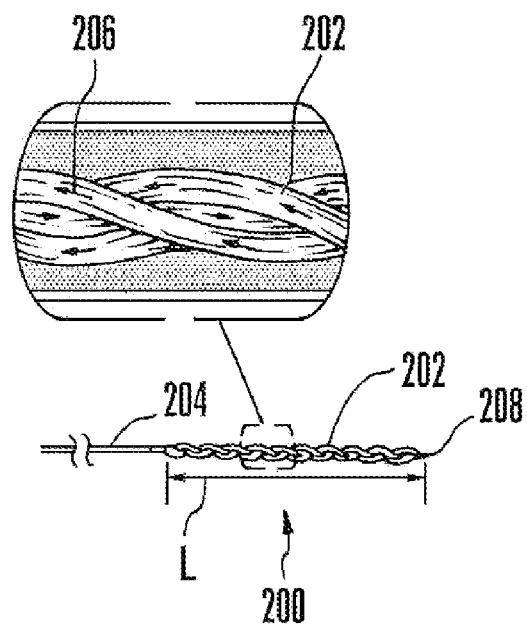
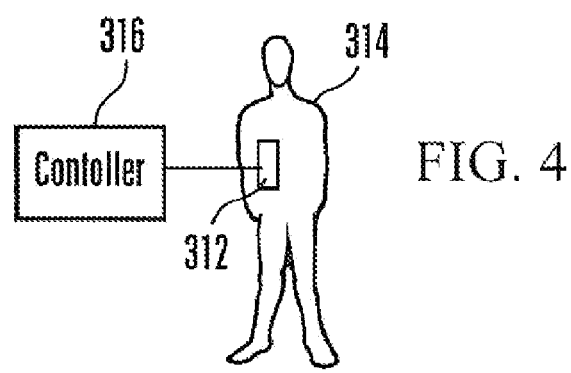
FIG. 4

SYSTEM AND METHOD FOR TREATING CARDIAC ARREST AND MYOCARDIAL INFARCTION

FIELD OF THE INVENTION

The present invention relates generally to systems for treating cardiac arrest and myocardial infarction.

BACKGROUND OF THE INVENTION

Intravascular catheters have been introduced for controlling patient temperature. Typically, a coolant such as saline is circulated through an intravascular heat exchange catheter, which is positioned in the patient's bloodstream, to cool or heat the blood as appropriate for the patient's condition. The coolant is warmed or cooled by a computer-controlled heat exchanger that is external to the patient and that is in fluid communication with the catheter.

For example, intravascular heat exchange catheters can be used to combat potentially harmful fever in patients suffering from neurological and cardiac conditions such as stroke, subarachnoid hemorrhage, intracerebral hemorrhage, cardiac arrest, and acute myocardial infarction, or to induce therapeutic hypothermia in such patients. Further, such catheters can be used to rewarm patients after, e.g., cardiac surgery or for other reasons. Intravascular catheters afford advantages over external methods of cooling and warming, including more precise temperature control and more convenience on the part of medical personnel.

The following U.S. patents, all of which are incorporated herein by reference, disclose various intravascular catheters/systems/methods: U.S. Pat. Nos. 6,419,643, 6,416,533, 6,409,747, 6,405,080, 6,393,320, 6,368,304, 6,338,727, 6,299,599, 6,290,717, 6,287,326, 6,165,207, 6,149,670, 6,146,411, 6,126,684, 6,306,161, 6,264,679, 6,231,594, 6,149,676, 6,149,673, 6,110,168, 5,989,238, 5,879,329, 5,837,003, 6,383,210, 6,379,378, 6,364,899, 6,325,818, 6,312,452, 6,261,312, 6,254,626, 6,251,130, 6,251,129, 6,245,095, 6,238,428, 6,235,048, 6,231,595, 6,224,624, 6,149,677, 6,096,068, 6,042,559.

As critically recognized by the present invention, the provision of magnesium sulfate in combination with hypothermia can effectively treat cardiac arrest and AMI.

SUMMARY OF THE INVENTION

A system for treating a patient includes a heat exchanger to induce hypothermia in the patient. The heat exchanger may be an external heat exchange pad or a heat exchange catheter configured for placement in a patient when heat exchange fluid is circulated through the catheter. A heat exchange controller supplies heat exchange fluid to the catheter and receives heat exchange fluid from the catheter in a closed circuit. A source of magnesium sulfate is used to deliver magnesium sulfate to the patient.

In one embodiment, the catheter has a heat exchange portion that is established by a balloon. In other embodiments, the heat exchange portion includes plural heat exchange fluid return tubes communicating with a supply lumen at a distal end of the catheter for carrying heat exchange fluid, with each return tube being formed spirally. In yet another embodiment, the heat exchange portion includes first and second elongated segments, each segment having an irregular exterior surface, and a flexible articulating joint connecting the first and second elongated segments.

In another aspect, a method for treating a patient includes inducing hypothermia in the patient using a closed loop heat exchange catheter, and simultaneously infusing magnesium sulfate to the patient.

In still another aspect, a system for treating a patient includes closed circuit heat exchange means and magnesium sulfate infusion means.

The details of the present invention, both as to its structure and operation, can best be understood in reference to the accompanying drawings, in which like reference numerals refer to like parts, and in which:

BRIEF DESCRIPTION OF THE DRAWINGS

FIG. 2 is a perspective view of an alternate catheter;

FIG. 3 is a perspective view of another alternate catheter, showing the distal portion of the catheter and an enlarged view of the heat exchange region; and FIG. 4 is a schematic view of an alternate embodiment using heat exchange pads.

DETAILED DESCRIPTION OF THE PREFERRED EMBODIMENT

Figure 1:
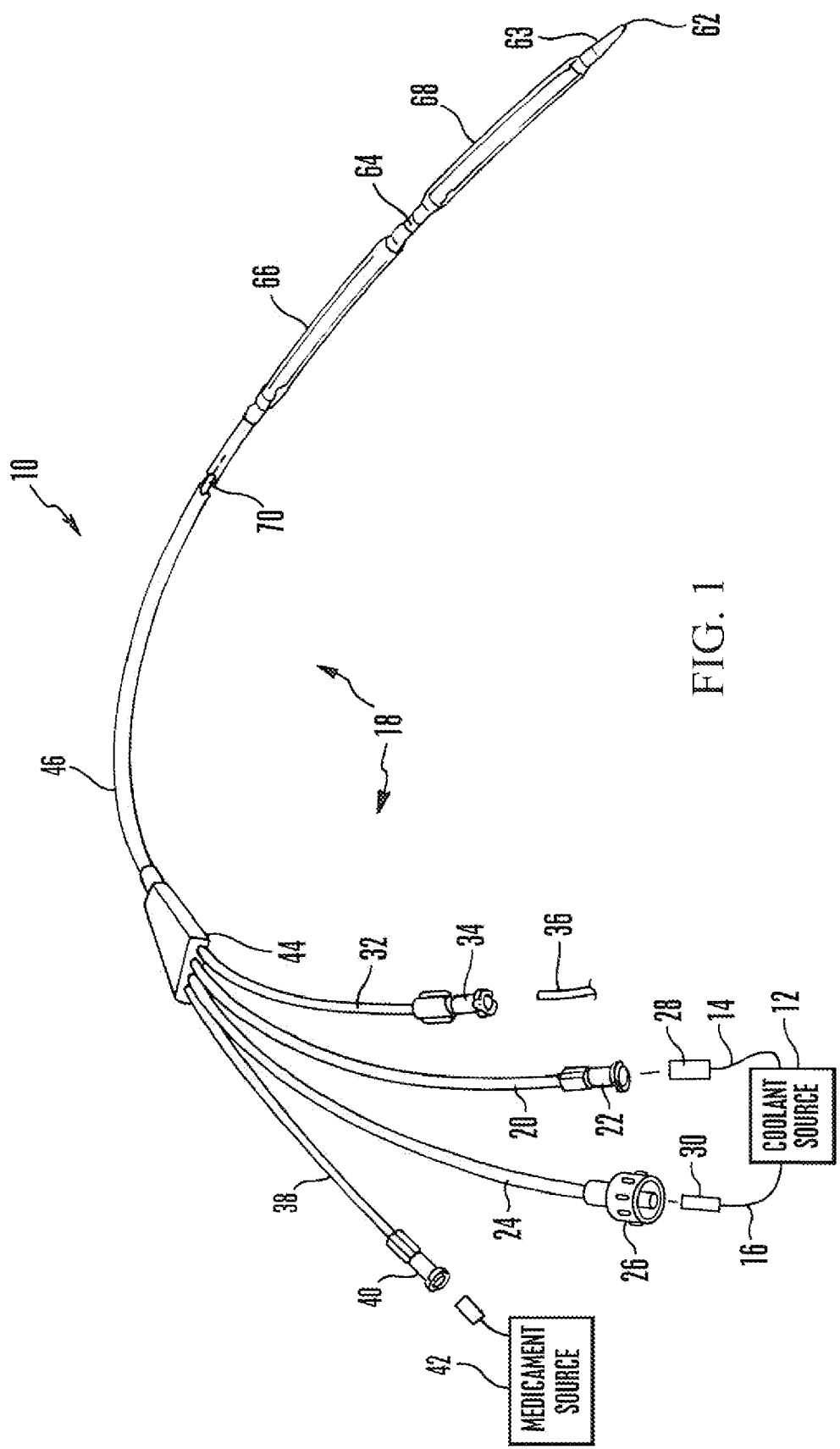
FIG. 1 is a perspective view of the present heat exchange catheter, schematically showing a medicament source and heat exchange fluid source in an exploded relationship with the catheter.

Referring initially to FIG. 1, a therapeutic catheter system, generally designated 10, is shown for establishing and maintaining hypothermia in a patient 11, or for attenuating a fever spike in a patient 11 and then maintaining normal body temperature in the patient. While FIG. 1 shows an exemplary embodiment of one heat exchange catheter, it is to be understood that the present invention applies to any of the catheters and accompanying heat exchange controllers disclosed in the above-referenced patents, including the helical shaped devices disclosed in Alsius' U.S. Pat. Nos. 6,451,045 and 6,520,933. Also, one of the spiral-shaped or convoluted-shaped catheters disclosed in Alsius' co-pending U.S. patent application Ser. No. 10/234,084, filed Aug. 30, 2002, for an "INTRAVASCULAR TEMPERATURE CONTROL CATHETER", and in Ser. No. 10/355,776, filed Jan. 31, 2003, both of which are incorporated herein by reference, can be used.

Commencing the description of the system 10 at the proximal end, as shown the exemplary non-limiting system 10 includes a heat exchange fluid source 12 that can be a water-bath heat exchange system or a TEC-based heat exchange system such as any of the systems disclosed in one or more of the above-referenced patents. Or, the source 12 can be a source of compressed gas. In any case, the heat exchange fluid source provides warmed or cooled heat exchange fluid such as saline or compressed gas through a heat exchange fluid supply line 14, and heat exchange fluid is returned to the source 12 via a heat exchange fluid return line 16. A catheter, generally designated 18, includes a source tube 20 terminating in a fitting such as a female Luer fitting 22. Also, the catheter 18 has a return tube 24 terminating in a fitting such a male Luer fitting 26. The fittings 22, 26 can be selectively engaged with complementary fittings 28, 30 of the lines 14, 16 to establish a closed circuit heat exchange fluid path between the catheter 18 and heat exchange fluid source 12.

Additionally, a non-limiting catheter 18 may include a guide wire and primary infusion tube 32 that terminates in a fitting such as a female Luer 34. A guide wire 36 can be advanced through the tube 32 in accordance with central venous catheter placement principles, or medicament or other fluid can be infused through the guide wire and primary infusion tube 32. Moreover, a secondary infusion tube 38 with female Luer fitting 40 can be selectively engaged with a medicament source 42 for infusing fluid from the source 42 through the secondary tube 38.

The source 42 may be a source of magnesium sulfate source. Thus, magnesium sulfate may be infused into the patient through the catheter. The source 42 may be an IV bag. Or, the source 42 may be a syringe. Other ways known in the art to deliver magnesium sulfate may also be used that do not necessarily include using the catheter to deliver the magnesium sulfate, e.g., a syringe can be used to inject magnesium sulfate directly into the patient through the skin.

As discussed further below, the tubes 20, 24, 32, 38 are held in a distally-tapered connector manifold 44. As also set forth further below, the connector manifold 44 establishes respective pathways for fluid communication between the tubes 20, 24, 32, 38 and respective lumens in a catheter body 46.

In any case, the connector manifold 44 establishes a pathway for fluid communication between the heat exchange fluid supply tube 20 and the heat exchange fluid supply lumen of the catheter. Likewise, the connector manifold 44 establishes a pathway for fluid communication between the heat exchange fluid return tube 24 and the heat exchange fluid return lumen. Further, the connector manifold 44 establishes a pathway for fluid communication between the guide wire and primary infusion tube 32, and the guide wire lumen, which can terminate at an open distal hole 62 defined by a distally tapered and chamfered distal tip 63 of the catheter body 46. Also, the connector manifold 44 establishes a pathway for fluid communication between the secondary infusion tube 38 and the secondary infusion lumen, which can terminate at an infusion port 64 in a distal segment of the catheter body 46. Additional ports can be provided along the length of the catheter.

An exemplary non-limiting catheter 18 has a distally-located heat exchange member for effecting heat exchange with the patient 11 when the catheter is positioned in the vasculature or rectum or other orifice of a patient. The heat exchange member can be any of the heat exchange members disclosed in the above-referenced patents. By way of example, a non-limiting catheter shown in FIG. 1 can have proximal and distal thin-walled heat exchange membranes 66, 68 that are arranged along the last fifteen or so centimeters of the catheter body 46 and that are bonded to the outer surface of the catheter body 46, with the infusion port 64 being located between the heat exchange membranes 66, 68. Thus, each preferred non-limiting heat exchange membrane is about six centimeters to seven and one-half centimeters in length, with the heat exchange membranes being longitudinally spaced from each other along the catheter body 46 in the preferred embodiment shown. Essentially, the heat exchange membranes 66, 68 extend along most or all of that portion of the catheter 46 that is intubated within the patient. The heat exchange membranes can be established by a medical balloon material.

The heat exchange membranes 66, 68 can be inflated with heat exchange fluid from the heat exchange fluid source 12 as supplied from the heat exchange fluid supply lumen, and heat exchange fluid from the heat exchange membranes 66, 68 is returned via the heat exchange fluid return lumen to the heat exchange fluid source 12.

If desired, a temperature sensor 70 such as a thermistor or other suitable device can be attached to the catheter 18 as shown. The sensor 70 can be mounted on the catheter 18 by solvent bonding at a point that is proximal to the membranes 66, 68. Or, the sensor 70 can be disposed in a lumen of the catheter 18, or attached to a wire that is disposed in a lumen of the catheter 18, with the sensor hanging outside the catheter 18. Alternatively, a separate temperature probe can be used, such as the esophageal probe disclosed in U.S. Pat. No. 6,290,717, incorporated herein by reference. As yet another alternative, a rectal probe or tympanic temperature sensor can be used. In any case, the sensor is electrically connected to the heat exchange fluid source 12 for control of the temperature of the heat exchange fluid as described in various of the above-referenced patents.

As envisioned by the present invention, the structure set forth above can be used in many medical applications to cool a patient and/or to maintain temperature in a normothermic or hypothermic patient, for purposes of improving the medical outcomes of, e.g., cardiac arrest patients, patients suffering from myocardial infarction or stroke, etc. As another example, head trauma can be treated by and after lowering and maintaining the patient's temperature below normal body temperature. Preferably, particularly in the case of myocardial infarction, the heat exchange portions are advanced into the vena cava of the patient 11 to cool blood flowing to the heart.

Now referring to FIG. 2, an alternate catheter 100 can include plural heat exchange elements 102. The heat exchange elements 102 can be established by one or more metal, preferably gold, hollow elongated segments that have external surfaces which have irregular exterior surfaces. Separating adjacent heat exchange elements 102 can be a flexible articulating joint 104, it being understood that the heat exchange elements 102 and joints 104 can be formed from a single piece of material such as plastic or metal, e.g., gold. The details of the heat exchange elements 102 and their configuration are set forth in U.S. Pat. No. 6,096,068, incorporated herein by reference. In any case, heat exchange fluid is circulated in a closed fluid communication loop between the heat exchange elements 102 and a heater/chiller to remove heat from the patient 12 to add heat to the patient to rewarm the patient after surgery or after the termination of therapeutic hypothermia treatment. When compressed gas is used as the heat exchange fluid, the gas is directed into the catheter, where it expands to cool the catheter and, thus, the patient.

FIG. 3 shows still another alternate heat exchange catheter 200. The catheter 200 shown in FIG. 3 can include plural heat exchange elements 202. The heat exchange elements 202 can be established by, e.g., three heat exchange fluid return tubes made of hollow plastic or metal, with each tube establishing a respective heat exchange fluid return lumen. A central heat exchange fluid supply lumen is established by a center tube 204. It is to be understood that the supply lumen conveys heat exchange fluid from a heater/chiller in a distal direction along the catheter 200, whereas the heat exchange elements 202 (the heat exchange fluid return tubes) convey heat exchange fluid back to the heater/chiller in a proximal direction as indicated by the arrows 206 in FIG. 3. Thus, heat exchange fluid is circulated in a closed fluid communication loop between the heat exchange elements 202 and heater/chiller to remove heat from the patient or to add heat to the patient to rewarm the patient after surgery or after the termination of therapeutic hypothermia treatment.

The heat exchange fluid return tubes are spirally formed around the center tube 204, and can be adhered thereto or not. That is, the preferred heat exchange elements 202 define spirals. The length "L" of the heat exchange region of the catheter 200 can be about 250 millimeters, with the pitch of the spiral heat exchange elements 202 being about 64 millimeters. In any case, the heat exchange fluid supply lumen terminates in a hollow distal tip 208, as do the lumens of the heat exchange elements 202. Accordingly, heat exchange fluid passes from the supply tube to the return tubes at the distal tip 208.

In operation, any one of the above-disclosed catheters is advanced (by, e.g., emergency response personnel) into the vasculature (preferably, the inferior vena cava or superior vena cava) or other cavity such as the rectum of a patient diagnosed as requiring temperature control. For example, a patient may be diagnosed with cardiac arrest, stroke, acute MI, or other malady for which therapeutic hypothermia may be indicated.

To cool the patient, the heat exchange fluid is cooled to below body temperature and circulated through the catheter as needed to reach a desired set point. Or, if the heat exchange fluid is gas, the gas is directed into the catheter where it expands and cools, cooling the catheter body. Magnesium sulfate is infused into the patient.

FIG. 4 shows that instead of inducing hypothermia using an intravascular catheter, one or more pads 312 may be positioned against the external skin of a patient 314 (only one pad 312 shown for clarity). The pad 312 may be any one of the pads disclosed in the following U.S. patents, all of which are incorporated herein by reference: U.S. Pat. Nos. 6,827,728, 6,818,012, 6,802,855, 6,799,063, 6,764,391, 6,692,518, 6,669,715, 6,660,027, 6,648,905, 6,645,232, 6,620,187, 6,461,379, 6,375,674, 6,197,045, and 6,188,930. The temperature of the pad 312 can be controlled by a controller 316 in accordance with principles set forth in the above patents to exchange heat with the patient 314, including to induce therapeutic mild or moderate hypothermia in the patient in response to the patient presenting with, e.g., cardiac arrest. Magnesium sulfate may then be injected into the patient prior to, during, or after inducing hypothermia in accordance with principles set forth above.

While the particular SYSTEM AND METHOD FOR TREATING CARDIAC ARREST AND MYOCARDIAL INFARCTION as herein shown and described in detail is fully capable of attaining the above-described objects of the invention, it is to be understood that it is the presently preferred embodiment of the present invention and is thus representative of the subject matter which is broadly contemplated by the present invention, that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more". All structural and functional equivalents to the elements of the above-described preferred embodiment that are known or later come to be known to those of ordinary skill in the art are expressly incorporated herein by reference and are intended to be encompassed by the present claims. Moreover, it is not necessary for a device or method to address each and every problem sought to be solved by the present invention, for it to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. §112, sixth paragraph, unless the element is expressly recited using the phrase "means for".

We claim:

1. A system for treating a patient, comprising:
  a heat exchange catheter configured for placement in the patient to induce hypothermia in the patient when heat exchange fluid is circulated through the catheter, the heat exchange fluid not entering the bloodstream of the patient; and
  a source of magnesium sulfate engageable with the patient to provide magnesium sulfate thereto through an infusion lumen of the catheter for treatment of cardiac arrest or myocardial infarction, wherein a distal portion of the catheter includes:
  at least first and second elongated segments, each segment having an irregular exterior surface; and
  a flexible articulating joint connecting the first and second elongated segments.

2. A method for treating a cardiac arrest patient, comprising:
  inducing hypothermia in the patient using a closed loop heat exchange catheter placed in a vein of the patient by circulating heat exchange fluid through the catheter without allowing the fluid to enter the blood; and
  infusing magnesium sulfate through the catheter into the patient, wherein the catheter includes:
  at least first and second elongated segments, each segment having an irregular exterior surface; and
  a flexible articulating joint connecting the first and second elongated segments.

3. The method of claim 2, wherein the catheter includes at least one balloon.

4. The method of claim 2, wherein the catheter includes plural heat exchange fluid return tubes communicating with a supply lumen at a distal end of the catheter for carrying heat exchange fluid, each return tube being formed spirally.

5. A system for treating a patient, comprising:
  heat exchange catheter means configured for engagement with the patient to exchange heat therewith; and
  magnesium sulfate infusion means defined by the catheter means for infusing extra magnesium sulfate to the patient, wherein the heat exchange means includes:
  at least first and second elongated segments, each segment having an irregular exterior surface; and
  a flexible articulating joint connecting the first and second elongated segments.

6. The system of claim 5, wherein the heat exchange means includes at least one balloon.

7. The system of claim 5, wherein the heat exchange means includes plural heat exchange fluid return tubes communicating with a supply lumen at a distal end of the heat exchange means for carrying heat exchange fluid, each return tube being formed spirally.

* * * * *